(12) United States Patent

Wiederhold et al.

(10) Patent No.: US 12,612,347 B2

(45) Date of Patent: Apr. 28, 2026

(54) METHOD FOR THE PREPARATION OF 1,2-PROPANEDIOL

(71) Applicant: Evonik Operations GmbH, Essen (DE)

(72) Inventors: Holger Wiederhold, Darmstadt (DE); David Bolz, Frankfurt (DE); Jürgen Berje, Hanau (DE)

(73) Assignee: Evonik Operations GmbH, Essen (DE)

( * ) Notice: Subject to any disclaimer, the term of this patent is extended or adjusted under 35 U.S.C. 154(b) by 494 days.

(21) Appl. No.: 18/249,982

(22) PCT Filed: Oct. 7, 2021

(86) PCT No.: PCT/EP2021/077678

§ 371 (c)(1),
(2) Date: Apr. 21, 2023

(87) PCT Pub. No.: WO2022/084052

PCT Pub. Date: Apr. 28, 2022

(65) Prior Publication Data

US 2023/0399280 A1 Dec. 14, 2023

(30) Foreign Application Priority Data

Oct. 21, 2020 (EP) ..................................... 20202970

(51) Int. Cl.
*C07C 29/48* (2006.01)
*C07C 29/80* (2006.01)

(52) U.S. Cl.
CPC .............. *C07C 29/48* (2013.01); *C07C 29/80* (2013.01)

(58) Field of Classification Search
CPC ......... C07C 29/48; C07C 29/74; C07C 41/05; C07C 31/205; C07C 43/04; B01J 27/188; B01J 31/0237; B01J 31/0239
See application file for complete search history.

(56) References Cited

U.S. PATENT DOCUMENTS 4,308,409 A 12/1981 Wu et al.
10,214,471 B2 2/2019 Wiederhold et al.
(Continued)

FOREIGN PATENT DOCUMENTS

KR 20180087337 A * 8/2018 ............. C07C 29/48
TW 2017/31805 A 9/2017
(Continued)

OTHER PUBLICATIONS

Machine translation of KR20180087337. (Year: 2018).*
(Continued)

*Primary Examiner* — Deborah D Carr
(74) *Attorney, Agent, or Firm* — Grüneberg Global IP, PLLC

(57) ABSTRACT

A method for preparing 1,2-propanediol involves reacting propene with hydrogen peroxide, in the presence of a phase transfer catalyst and a heteropolytungstate, in a liquid two phase reaction mixture with an organic phase containing an alkylaromatic hydrocarbon solvent. The method then involves separating the reaction mixture into an aqueous phase containing 1,2-propanediol and an organic phase, recycling the oxygen depleted organic phase to the reaction, and recovering 1,2 propanediol from the aqueous phase. The reaction and separation are carried out in liquid flooded vessels at a pressure high enough to suppress desorption of gas from the liquid reaction mixture. The separated organic phase is contacted with a stream of a non-flammable gas to desorb from 10 to 75% of the oxygen dissolved in the organic phase into the stream of non-flammable gas, before (Continued)

recycling the organic phase which purges oxygen safely with little loss of propene.

20 Claims, 1 Drawing Sheet

(56) References Cited

U.S. PATENT DOCUMENTS

| | | | |
|---|---|---|---|
| 2012/0142950 | A1 | 6/2012 | Teles et al. |
| 2018/0354878 | A1 | 12/2018 | Wiederhold et al. |
| 2020/0109125 | A1 | 4/2020 | Hofen et al. |

FOREIGN PATENT DOCUMENTS

| | | |
|---|---|---|
| WO | 2017/089075 | 6/2017 |
| WO | 2022/084047 | 4/2022 |
| WO | 2022/084048 | 4/2022 |
| WO | 2022/084049 | 4/2022 |
| WO | 2022/084050 | 4/2022 |
| WO | 2022/084055 | 4/2022 |
| WO | 2022/084056 | 4/2022 |
| WO | 2022/084057 | 4/2022 |
| WO | 2022/084060 | 4/2022 |
| WO | 2022/084061 | 4/2022 |
| WO | 2022/084062 | 4/2022 |

OTHER PUBLICATIONS

International Search report issued Dec. 23, 2021, in PCT/EP2021/077678, 5 pages.
Written Opinion issued Dec. 23, 2021, in PCT/EP2021/077678, 8 pages.
U.S. Appl. No. 18/249,984, filed Apr. 21, 2023, Wiederhold et al.
U.S. Appl. No. 18/249,724, filed Apr. 19, 2023, Wiederhold et al.
U.S. Appl. No. 18/249,980, filed Apr. 21, 2023, Wiederhold et al.
U.S. Appl. No. 18/249,584, filed Apr. 19, 2023, Wiederhold et al.
U.S. Appl. No. 18/249,695, filed Apr. 19, 2023, Wiederhold et al.
U.S. Appl. No. 18/249,729, filed Apr. 19, 2023, Bolz et al.
U.S. Appl. No. 18/249,908, filed Apr. 20, 2023, Wiederhold et al.
U.S. Appl. No. 18/249,660, filed Apr. 19, 2023, Wiederhold et al.
U.S. Appl. No. 18/249,906, filed Apr. 20, 2023, Wiederhold et al.
U.S. Appl. No. 18/249,825, filed Apr. 20, 2023, Wiederhold et al.
U.S. Pat. No. 10,214,471, Feb. 26, 2019, 2018/0354878, Wiederhold et al.
Indian Office Action dated Jul. 19, 2023, in Indian Application No. 202347034266, with English translation, 5 pages.
English translation of the Saudi Arabian 1st Substantive Examination Report, in Saudi Arabian Application No. 523440415.

* cited by examiner

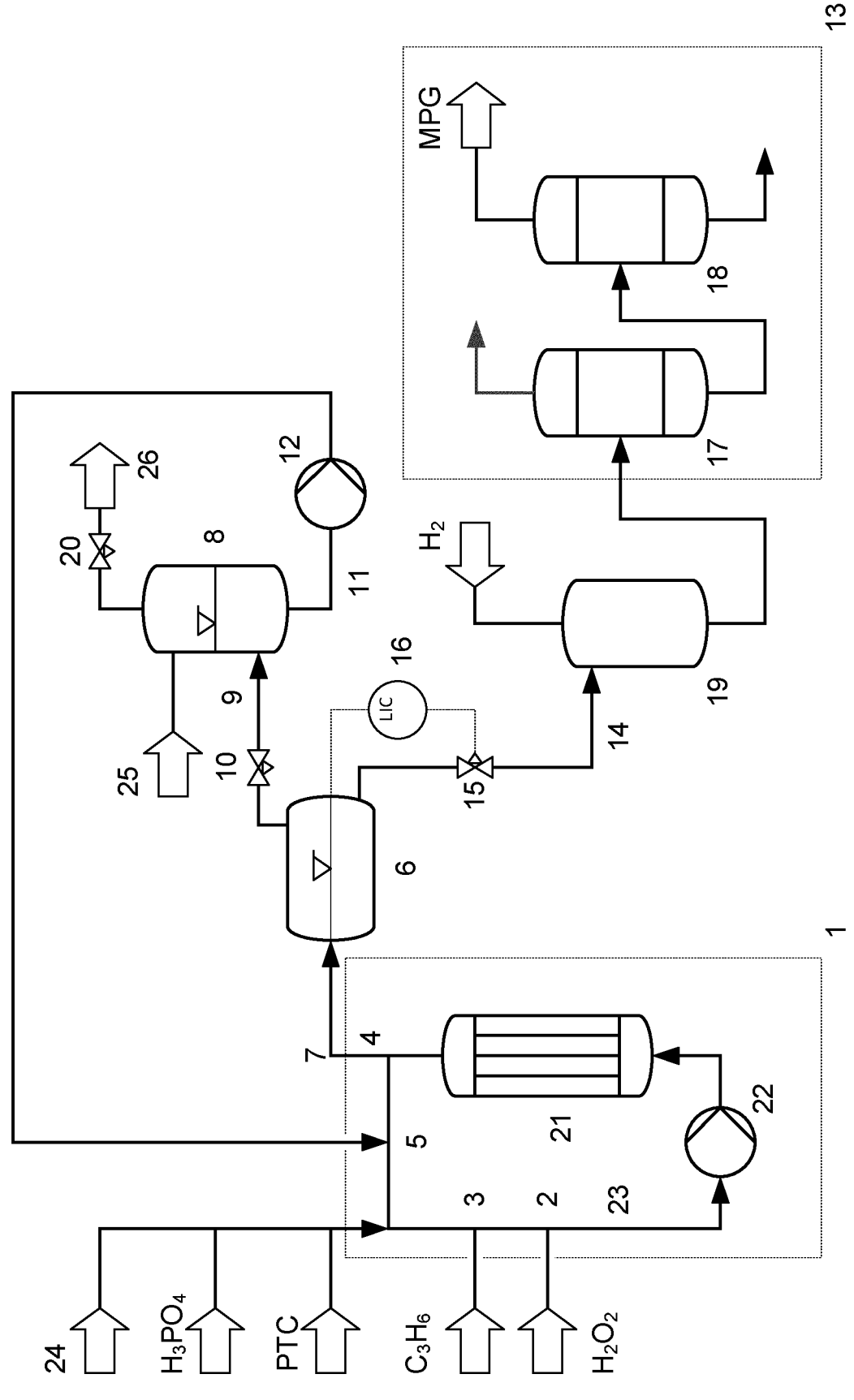

METHOD FOR THE PREPARATION OF 1,2-PROPANEDIOL

CROSS-REFERENCE TO RELATED APPLICATIONS

This application is a National Stage entry under § 371 of International Application No. PCT/EP2021/077678, filed on Oct. 7, 2021, and which claims the benefit of priority to European Application No. 20202970.8, filed on Oct. 21, 2020. The content of each of these applications is hereby incorporated by reference in its entirety.

BACKGROUND OF THE INVENTION

Field of the Invention

The present invention relates to a method for the preparation of 1,2-propanediol by reacting propene with hydrogen peroxide.

Description of Related Art

In a well-established process used in the industry, 1,2-propanediol is prepared by reacting propene oxide with water. Propene oxide can be made on an industrial basis using the HPPO process comprising the reaction of propene with hydrogen peroxide in the presence of a titanium zeolite catalyst and an organic solvent. Propene oxide is then isolated and purified prior to the step of reacting it with water to make 1,2-propanediol.

WO 2017/089075 discloses a method for producing 1,2-propanediol from propene and hydrogen peroxide comprising: a) reacting propene with hydrogen peroxide in the presence of a catalyst mixture comprising a phase transfer catalyst and a heteropolytungstate, wherein the reaction is carried out in a liquid mixture comprising an aqueous phase with a maximum pH of 6 and an organic phase, b) dividing the two-phase mixture from step a) into an aqueous phase and an organic phase containing propylene oxide, c) returning the propylene oxide contained in the separated organic phase into the reaction from step a) and d) separating 1,2-propanediol from the aqueous phase separated in step b). Step b) is preferably carried out in the presence of a gas phase. Preferably, an inert gas is introduced in step b) and a gas stream is withdrawn to keep the oxygen content of this gas phase at below 7 vol.-% to prevent formation of a combustible gas phase.

Example 8 of WO 2017/089075 discloses an embodiment of the method where step a) is carried out at a temperature of 78° C. and a pressure of 4.2 MPa and step b) is carried out in two consecutive phase separators operated at 1.6 MPa, where the aqueous phase is separated from the organic phase and a gas phase in the first phase separator and the inert gas is introduced into the second phase separator where the organic phase is separated from the gas phase.

In the process disclosed in the description and the examples of WO 2017/089075, a gas phase may form in the reactor where propene is reacted with hydrogen peroxide or during separation of the two liquid phases as described in example 8 of WO 2017/089075. This gas phase may contain oxygen, formed by decomposition of hydrogen peroxide in step a), at a level which makes the gas phase flammable and presents an explosion hazard.

SUMMARY OF THE INVENTION

The inventors of the present invention have now found that the process of WO 2017/089075 can be operated more safely by carrying out steps a) and b) in vessels which are flooded by the liquid reaction mixture and applying a pressure high enough to suppress desorption of gas from the liquid reaction mixture in these steps followed by desorption of oxygen from the separated organic phase into a non-flammable gas such as nitrogen. The inventors have also found that only a part of the oxygen dissolved in the organic phase ($P_o$) needs to be desorbed to prevent formation of a flammable gas phase in steps a) and b) and that desorbing only a part of the dissolved oxygen strongly reduces the amount of propene which is desorbed along with the oxygen to only a few percent of the propene fed to step a). This allows an economic operation of the process with little or no extra equipment for recovery of non-reacted propene. The inventors have further found that this also allows operating the process with a chemical grade propene containing from 1 to 8% by volume of propane, enriching propane in the recycle stream to a mass fraction in the combined amount of propane and propene of from 0.2 to 0.7 and purging the propane with the off-gas of the oxygen desorption, which removes propane from the process with little loss of propene without requiring a step of separating propane and propene.

Subject of the invention is therefore a method for the preparation of 1,2-propanediol comprising the steps:

a) reacting propene with hydrogen peroxide at a temperature of from 50 to 110° C. in the presence of a catalyst mixture comprising a phase transfer catalyst and a heteropolytungstate in a liquid reaction mixture comprising an aqueous phase with a maximum apparent pH of 6 and an organic phase comprising an alkylaromatic hydrocarbon solvent;

b) separating the reaction mixture obtained in step a) into an aqueous phase ($P_a$) comprising 1,2-propanediol and an organic phase ($P_o$) comprising non-reacted propene, the alkylaromatic hydrocarbon solvent and dissolved oxygen from hydrogen peroxide decomposition;

c) contacting the organic phase ($P_o$) separated in step b) with a stream of a non-flammable gas at a flow rate of non-flammable gas, a temperature and a pressure effecting desorption of from to 75% of the oxygen dissolved in the organic phase ($P_o$) into the stream of non-flammable gas, providing an oxygen depleted organic phase ($P_d$) and an off-gas comprising the non-flammable gas and desorbed propene and oxygen;

d) recycling at least a part of the oxygen depleted organic phase ($P_d$) to the reaction step a); and e) recovering 1,2-propanediol from the aqueous phase ($P_a$);

wherein the mass ratio of alkylaromatic hydrocarbon solvent introduced to step a) to hydrogen peroxide introduced to step a) is from 4:1 to 30:1 and steps a) and b) are carried out in vessels flooded by the liquid reaction mixture at a pressure high enough to suppress desorption of gas from the liquid reaction mixture.

A further subject of the invention is a facility for preparing 1,2-propanediol, comprising:

a) a cooled loop reactor (1) comprising an inlet (2) for hydrogen peroxide, an inlet (3) for propene, an outlet (4) for reaction mixture, and at least one recycle stream inlet (5);

b) a phase separator (6) comprising an inlet, a first outlet for separated aqueous phase and a second outlet for separated organic phase, the inlet being connected by a conduit (7) to the outlet of the loop reactor (1) for receiving reaction mixture;

c) an oxygen desorption unit (8) having a liquid inlet, an inlet for inert gas, an off-gas outlet and a liquid outlet, the liquid inlet being connected by a conduit (9), comprising a pressure retention valve (10), to the second outlet of the phase separator (6) for receiving the separated organic phase and the liquid outlet being connected by a conduit (11) comprising a recycle pump (12) to a recycle stream inlet of the loop reactor; and d) a separation unit (13), having an inlet connected by a conduit (14), comprising a control valve (15), to the first outlet of the phase separator (6), an outlet for separated water, an outlet for separated 1,2-propanediol and an outlet for by-products.

BRIEF DESCRIPTION OF DRAWINGS

The FIGURE shows an embodiment of the facility of the invention comprising a separation unit with two distillation columns and an additional hydrogenation unit.

DETAILED DESCRIPTION OF THE INVENTION

In the method of the present invention, propene is reacted in a step a) with hydrogen peroxide in the presence of a catalyst mixture comprising a phase transfer catalyst and a heteropolytungstate. This reaction is carried out at a temperature of from 50 to 110° C. in a liquid reaction mixture which comprises an aqueous phase with a maximum apparent pH of 6 and an organic phase comprising an alkylaromatic hydrocarbon solvent.

Propene can be used in pure form or in a mixture with propane, wherein the proportion of propane may be up to 20 mol-%. The proportion of propane in the propene feedstock is preferably in the range of from 1 to 8 mol-%. Propene is preferably employed in a molar excess to hydrogen peroxide. Preferably, the molar ratio of propene introduced to step a) to hydrogen peroxide introduced to step a) is from 1.2:1 to 5:1, more preferably from 1.5:1 to 3:1. The propene feedstock is preferably introduced into step a) as a liquid.

Hydrogen peroxide is preferably used in the form of an aqueous solution, preferably with a hydrogen peroxide content of 10 to 80% by weight, particularly preferably 30 to 70% by weight. Any commercially available grade of aqueous hydrogen peroxide solutions can be used. A crude hydrogen peroxide product obtained in the extraction stage of the anthraquinone process for producing hydrogen peroxide may also be used.

The catalyst mixture used in step a) comprises a heteropolytungstate. The heteroatom is preferably phosphorus or arsenic and is particularly preferably phosphorus, i.e. the heteropolytungstate is particularly preferably a polytungstophosphate. Heteropolytungstates are well known to a person skilled in the art. Preferred polytungstophosphates have a molar ratio of phosphorus to tungsten in the range of from 1:2 to 1:12. The polytungstophosphate is preferably generated in situ by combining phosphoric acid and sodium tungstate, which can be carried out in the liquid reaction mixture itself or prior to adding the polytungstophosphate to the liquid reaction mixture. Phosphoric acid and sodium tungstate are preferably employed at a molar ratio of phosphorus to tungsten in the range of from 1:2 to 10:1, preferably from 4:1 to 8:1. The heteropolytungstate reacts with hydrogen peroxide in the liquid reaction mixture to form peroxotungstates and peroxotungstophosphates, for example $PO_4[WO(O_2)_2]_4^{3-}$ and $HPO_4[WO(O_2)_2]_2^{2-}$ as well as partially protonated forms thereof, which are presumably the catalytically active species for oxidizing propene.

The catalyst mixture used in step a) also comprises a phase transfer catalyst. The phase transfer catalyst comprises a cation or a compound which forms a cation in the aqueous phase, whereby the cation can form a salt with a peroxotungstate or heteropolyperoxotungstate, which salt is soluble in the organic phase of the liquid reaction mixture. The phase transfer catalyst preferably comprises a singly-charged cation or a compound which forms a singly-charged cation in the aqueous phase. Suitable as phase transfer catalyst are tertiary amines, tertiary and quaternary ammonium salts, and quaternary phosphonium salts. Suitable counterions for tertiary and quaternary ammonium salts are the anions chloride, bromide, nitrate, sulphate, hydrogen phosphate, dihydrogen phosphate, methyl sulfonate, methyl sulphate and ethyl sulphate. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, where the molar ratio refers to the cations or compounds forming cations in the employed phase transfer catalyst and to the employed amount of tungsten.

In a preferred embodiment, the phase transfer catalyst is a tertiary amine or a tertiary or a quaternary ammonium salt which comprises in total at least 12 carbon atoms, preferably from 12 to carbon atoms. Preferred are tetraalkylammonium salts. Suitable tertiary amines are for example dodecyldimethylamine, hexadecyldimethylamine, octadecyldimethylamine, tributylamine and trioctylamine. Suitable tertiary ammonium salts are the protonation products of these teriary amines. Suitable quaternary ammonium salts are for example dodecyltrimethylammonium salts, hexadecyltrimethylammonium salts, octadecyltrimethylammonium salts, methyltributylammonium salts and methyltrioctylammonium salts. More preferably, the phase transfer catalyst comprises a tertiary or quaternary ammonium ion having the structure $R^1R^2R^3NR^{4+}$, wherein $R^1$, $R^2$ and $R^3$ are the same or different and are each selected from alkyl groups having from 8 to 10 carbon atoms and $R^4$ is hydrogen or methyl. Most preferably, the phase transfer catalyst comprises methyltri(octylidecyl)ammonium methylsulfate (CAS No. 2387913-24-6).

In another preferred embodiment, the phase transfer catalyst comprises at least one salt having a tertiary or quaternary ammonium ion of the structure $R^1R^2R^3R^4N^+$, where $R^1$ is a $Y—O(C{=}O)R^5$ group with Y being $CH_2CH_2$, $CH(CH_3)CH_2$ or $CH_2CH(CH_3)$ and $R^5$ being an alkyl group or alkenyl group having 11 to 21 carbon atoms,
$R^2$ is hydrogen or an alkyl group having 1 to 4 carbon atoms, and $R^3$ and $R^4$ are each independently $R^1$, an alkyl group having 1 to 4 carbon atoms or $Y—OH$. Preferred are quaternary ammonium salts with methylsulphate as the counterion, where $R^2$ is a methyl group and $R^5$ is a linear alkyl group or alkenyl group. Particularly preferred are the salts $(CH_3)_3N^+CH_2CH_2O(C{=}O)R^5$ $CH_3OSO_3^-$, $(CH_3)_2N^+$ $(CH_2CH_2OH)(CH_2CH_2O(C{=}O)R^5)$ $CH_3OSO_3^-$, $(CH_3)_2N^+$ $(CH_2CH_2O(C{=}O)R^5)_2$ $CH_3OSO_3^-$, $CH_3N^+(CH_2CH_2OH)_2$ $(CH_2CH_2O(C{=}O)R^5)$ $CH_3OSO_3^-$, $CH_3N^+(CH_2CH_2OH)$ $(CH_2CH_2O(C{=}O)R^5)_2$ $CH_3OSO_3^-$, $CH_3N^+(CH_2CH_2O(C{=}O)R^5)_3$ $CH_3OSO_3^-$, $(CH_3)_3N^+CH_2CH(CH_3)O(C{=}O)$ $R^5$ $CH_3OSO_3^-$, $(CH_3)_2N^+(CH_2CH(CH_3)OH)(CH_2CH(CH_3)$ $O(C{=}O)R^5)$ $CH_3OSO_3^-$ and $(CH_3)_2N^+(CH_2CH(CH_3)O$ $(C{=}O)R^5)_2$ $CH_3OSO_3^-$, in which $R^5$ is in each case a linear alkyl group or alkenyl group having 11 to 21 carbon atoms. Most preferred is the salt $(CH_3)_2N^+(CH_2CH(CH_3)O(C{=}O)$ $R^5)_2$ $CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or triisopropanolamine with a fatty acid and subsequent quaternization with dimethyl sulphate. These phase transfer catalysts have the advantage that they are readily biodegradable, unlike tetraalkylammonium salts, and can be introduced into a biological treatment plant without further pretreatment. The salts with methylsulphate as anion are also less corrosive than tetraalkylammonium halides.

The reaction of step a) is carried out in a liquid reaction mixture which comprises two liquid phases, an aqueous phase with a maximum apparent pH of 6 and an organic phase comprising an alkylaromatic hydrocarbon solvent. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the aqueous phase of the reaction mixture, which comprises hydrogen peroxide and glycols, is different than the normal potential in pure water. The apparent pH of the aqueous phase is preferably maintained in the range from 1.0 to 3.5, particularly preferably in the range from 2.0 to 3.0. The apparent pH can be maintained in this range by addition of acid, preferably sulphuric acid or phosphoric acid, or by addition of base, preferably aqueous sodium hydroxide solution. Adjusting the apparent pH in the preferred range provides high selectivity for 1,2-propanediol and prevents enriching propene oxide in the aqueous phase, which simplifies the subsequent separation of propylene glycols from the aqueous phase.

When a catalyst mixture comprising a polytungstophosphate is used in step a), the reaction is preferably carried out in the presence of phosphoric acid. Phosphoric acid may be used to provide an apparent pH of the aqueous phase ($P_a$) of the reaction mixture of from 1.0 to 3.5, preferably of from 2.0 to 3.0. The concentration of phosphoric acid and phosphates in the aqueous phase ($P_a$) of the reaction mixture is preferably from 0.2 to 0.8% by weight, calculated as $PO_4^{3-}$ relative to the mass of the aqueous phase. Phosphoric acid may also be present from in situ formation of a polytungstophosphate in the aqueous phase ($P_a$) of the reaction mixture as described above.

The amount of dipropylene glycol formed a s a byproduct in step a) can be adjusted by adjusting the weight ratio of hydrogen peroxide to water fed to step a). The weight ratio of hydrogen peroxide to water is preferably varied within the range of from 0.05 to 1.5, more preferably from 0.10 to 0.7 and most preferably from 0.15 to 0.45.

The reaction of step a) is carried out in a reaction mixture which comprises an organic phase comprising an alkylaromatic hydrocarbon solvent. The alkylaromatic hydrocarbon solvent preferably has a boiling point of more than 100° C., more preferably of from 120° C. to 250° C., and preferably has a solubility in water of less than 250 mg/kg at 20° C. Suitable alkylated aromatic hydrocarbons are, for example, toluene, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3,5-trimethylbenzene (mesitylene), 1-ethyl-2-methylbenzene, 1-ethyl-3-methylbenzene and 1-ethyl-4-methylbenzene and n-propylbenzene. Preferably, the alkylaromatic hydrocarbon solvent comprises more than 50% by weight, particularly preferably more than 80% by weight, of alkylated aromatic hydrocarbons having 7 to 12 carbon atoms. The use of the alkylaromatic hydrocarbon solvent enables extracting most of the heteropolytungstate into the organic phase of the reaction mixture and recycling them, which allows for operating the method of the invention without a need for recovering heteropolytungstate from the aqueous phase of the reaction mixture of step a). The phase transfer catalyst, the molar ratio of phase transfer catalyst to heteropolytungstate, the molar ratio of heteroatom of the heteropolytungstate to tungsten, the molar ratio of propene to hydrogen peroxide and the amount of solvent are then preferably selected to transfer as much as possible of the tungsten present in the liquid reaction mixture into the organic phase. The alkylaromatic hydrocarbon solvent also provides sufficient solubility of oxygen in the organic phase.

The phase transfer catalyst, the heteropolytungstate and the solvent can be added in step a) of the method of the present invention separately or in the form of mixtures containing two or all three of these components. Preferably, the phase transfer catalyst and the heteropolytungstate are added dissolved in an organic phase comprising the alkylaromatic hydrocarbon solvent.

The reaction is conducted at a temperature in the range of from 50 to 110° C., more preferably 60 to 100° C. and particularly preferably 70 to 90° C. A reaction temperature of at least 50° C. provides sufficient reaction rate for propene oxidation which allows achieving a desired hydrogen peroxide conversion and limiting the reaction temperature to no more than 110° C. keeps decomposition of hydrogen peroxide to molecular oxygen at a low level.

The reaction of step a) may be carried out in batch or continuously, with a continuous reaction being preferred. The concentration of hydrogen peroxide in the aqueous phase is preferably maintained in the range of 0.1 to 5% by weight, particularly preferably 0.5 to 3% by weight. The concentration of hydrogen peroxide can be adjusted in this range by appropriate selection of the reaction temperature, the molar ratio of propene to hydrogen peroxide and the residence time of the liquid mixture in the reactor in which the reaction takes place. Keeping the hydrogen peroxide concentration within this range keeps hydrogen peroxide decomposition to oxygen at low levels and reduces the pressure necessary for keeping the oxygen dissolved in the organic phase of the reaction mixture. The residence time of the reaction mixture is preferably adjusted to maintain a hydrogen peroxide conversion in the range of from 80 to 99%.

The mass ratio of alkylaromatic hydrocarbon solvent introduced to step a) to hydrogen peroxide introduced to step a) is selected in the range of from 4:1 to 30:1. Using an amount of alkylaromatic hydrocarbon solvent within this range allows for keeping all of the molecular oxygen, formed in step a) by decomposition of hydrogen peroxide, dissolved in the organic phase of the reaction mixture.

The reaction of step a) is carried out in a vessel which is flooded by the liquid reaction mixture. For this purpose, the reaction of step a) is carried out at a pressure high enough to suppress desorption of gas, such as gaseous propene or oxygen, from the liquid reaction mixture. The reaction pressure is preferably higher than the vapor pressure of propene at the reaction temperature to ensure that all of the propene stays dissolved in the organic phase of the liquid reaction mixture. The reaction of step a) is preferably carried out continuously in a loop reactor which is flooded by the liquid reaction mixture, feeding only liquid feed streams to the loop reactor. Reaction mixture exiting the loop reactor is preferably passed through an additional pipe reactor flooded with liquid reaction mixture before it is passed to step b) of the method in order to increase hydrogen peroxide conversion.

During the reaction of step a), the liquid reaction mixture is preferably mixed in order to generate a large phase interface between the aqueous phase and the organic phase. For this purpose, the reaction is preferably carried out continuously in a loop reactor which has fixed internals in a tubular section and the liquid mixture is passed through the loop reactor at a flow rate which generates a turbulent flow at the internals. Baffles, static mixing elements, structured packings or random packings can be used as internals for this purpose. In combination to these internals or as an alternative, heat exchangers, such as plate heat exchangers or tube bundle heat exchangers, may be used, in which turbulent flow is generated, for example between the plates of a plate heat exchanger or in the tubes of a tube bundle heat exchanger.

Preferably, all or a part of the reaction heat generated in step a) is removed while the reaction proceeds, preferably by cooling the reaction mixture in a heat exchanger. More preferably, the reaction is carried out continuously in a loop reactor which comprises a heat exchanger within the reactor loop for cooling the reaction mixture.

In step b) of the method of the present invention, the liquid reaction mixture provided by step a) is separated into an aqueous phase $(P_a)$ comprising 1,2-propanediol and an organic phase $(P_o)$ comprising non-reacted propene, the alkylaromatic hydrocarbon solvent and dissolved oxygen from hydrogen peroxide decomposition. The separation of the two-phase liquid reaction mixture provided by step a) is carried out in one or several vessels which are flooded by the two-phase liquid reaction mixture. The separation of the two-phase reaction mixture is preferably carried out in a settler vessel. The two-phase reaction mixture is preferably passed through a coalescer element comprising a structured packing or a random packing with a surface wetted by the dispersed phase of the two-phase mixture in order to achieve a more complete separation.

The separation of step b) is carried out at a pressure high enough to suppress desorption of gas, such as gaseous propene or oxygen, from the liquid reaction mixture. If the separation of step b) is carried out at the same temperature as step a), the pressure in step b) is preferably the same as or higher than in step a). Preferably, the separation of step b) is carried out at a lower temperature than the reaction temperature employed in step a).

The aqueous phase $(P_a)$ separated in step b) typically comprises water, unreacted hydrogen peroxide and the reaction product 1,2-propanediol. The aqueous phase typically also contains dipropylene glycol and tripropylene glycol as well as reaction byproducts, such as 1-hydroperoxy-2-propanol and 2-hydroperoxy-1-propanol formed by reaction of propene oxide with hydrogen peroxide, and formic acid, acetic acid and hydroxyacetone formed by further oxidation of 1,2-propanediol. The aqueous phase may also comprise phosphoric acid and may further contain sodium salts of phosphoric acid if a polytungstophosphate generated in situ by combining phosphoric acid and sodium tungstate is used in step a). The organic phase $(P_o)$ comprises the alkylaromatic hydrocarbon solvent as well as unreacted propene and propene oxide that is formed as intermediate when propene is reacted with hydrogen peroxide and has not been hydrolyzed to 1,2-propanediol. The organic phase $(P_o)$ further comprises dissolved oxygen resulting from hydrogen peroxide decomposition in step a). The organic phase $(P_o)$ typically also comprises one or more salts formed of the heteropolytungstate and the cation of the phase transfer catalyst. The organic phase $P_o$ will also comprise propane, if the propene starting material contains propane.

In step c) of the method of the present invention, the organic phase $(P_o)$ which has been separated in step b) is contacted with a stream of a non-flammable gas. The flow rate of non-flammable gas, the temperature and the pressure are adjusted in step c) to desorb from 10 to 75% and preferably from 30 to 60% of the oxygen dissolved in the organic phase $(P_o)$ into the stream of non-flammable gas. This way, step c) provides an oxygen depleted organic phase $(P_d)$ and an off-gas comprising the non-flammable gas and desorbed propene and oxygen. The proportion of dissolved oxygen which is desorbed into the stream of non-flammable gas can be increased by increasing the flow rate of non-flammable gas, increasing the temperature or decreasing the pressure used in step c) or by any combination of these measures. A decrease of the proportion of dissolved oxygen which is desorbed into the stream of non-flammable gas can be achieved by decreasing the flow rate of non-flammable gas, decreasing the temperature or increasing the pressure used in step c) or by any combination of these measures. Step c) is preferably carried out at a temperature of the organic phase $(P_o)$ of from 20 to 80° C. Compared to a complete or essentially complete desorption of oxygen from the organic phase $(P_o)$, desorbing only a part of the oxygen dissolved in the organic phase $(P_o)$ has the advantage that much less propene is desorbed into the stream of non-flammable gas along with the oxygen. This way, the loss of propene with the purge of oxygen from the process can be reduced to a level of only a few percent of the propene introduced with the propene feedstock and the method becomes resource efficient and economical without additional steps for recovering propene from the off-gas produced in step c).

Nitrogen, argon, carbon dioxide and any mixture thereof may be used as non-flammable gas, with nitrogen being preferred. The flow rate of non-flammable gas, the temperature and the pressure are preferably adjusted to provide an oxygen concentration in the off-gas of from 1 to 11 mol-%.

Step c) may be carried out in a vessel by introducing the stream of non-flammable gas into a gas space present above the organic phase $(P_o)$ or preferably by passing the non-flammable gas through the organic phase $(P_o)$ to strip oxygen from the organic phase $(P_o)$, for example by introducing non-flammable gas at the bottom of the vessel. In a preferred embodiment, the desorption of oxygen is carried out with counter current flow of non-flammable gas and organic phase $(P_o)$. Such counter current flow can be achieved in a bubble column or a trickle bed with down flow of the organic phase $(P_o)$ and counter current flow of the stream of non-flammable gas.

In step d) of the method of the present invention, at least a part and preferably all of the oxygen depleted organic phase $(P_d)$ provided in step c) is recycled to the reaction step a). Thereby, non-reacted propene and propene oxide present in the organic phase $(P_o)$ are recycled to step a) in order to achieve a complete conversion of propene to 1,2-propanediol, dipropylene glycol and tripropylene glycol. Preferably, the heteropolytungstate present in the organic phase $(P_o)$ is also recycled into step a), and it is particularly preferred to recycle substantially all of the catalyst mixture that is present in the organic phase into step a).

Steps a) to d) of the method of the present invention are preferably carried out continuously. The fraction of oxygen desorbed in step c) is then preferably adjusted to remove the same amount of oxygen with the off-gas of step c) as formed by decomposition of hydrogen peroxide in step a). Preferably, the parameters for desorbing oxygen in step c) are selected to maintain an oxygen concentration in the organic phase of the reaction mixture of step a) at steady state conditions which is from 20 to 80% of the oxygen saturation concentration in the organic phase of the reaction mixture at the temperature and pressure used in step a).

In a preferred embodiment, step a) is carried out with a propene feedstock containing from 1 to 8 mol-% of propane and in step c) the flow rate of non-flammable gas, the temperature and the pressure are adjusted to provide an off gas with a mass ratio of propane to the combined amount of propane and propene of from 0.2 to 0.7. This can be achieved by adjusting the parameters in the desorption of step c) to minimize the loss of propene with the purge of oxygen, which will lead to an enrichment of propane in the process by recycling propane with the oxygen depleted organic phase ($P_d$) to step a). This way, propane can be enriched in the process to a level where all the propane introduced with the propene feedstock will be purged from the process with the off-gas of step c) along with only a few percent of the propene introduced with the propene feedstock. This allows form operating the method of the invention in an efficient and economical manner without an additional step for separating propane from propene.

In step e) of the method of the present invention, 1,2-propanediol is recovered from the aqueous phase ($P_a$) separated in step b), preferably by distillation. Preferably, 1,2-propanediol and higher propylene glycols, like dipropylene glycol and tripropylene glycol, are recovered by a sequence of distillation steps, such as a multi-step distillation with the first distillation step and optionally further distillation steps providing an overhead product comprising water and a bottoms product which is passed to the next distillation step, and a distillation step providing an overhead product comprising 1,2-propanediol and a residuals bottoms product which is preferably subjected to at least one further distillation step. Most preferably, a sequence of distillation steps as described in Ullmann's Encyclopedia of Industrial Chemistry, online edition, entry "Propanediols", page 4, DOI 10.1002/14356007.a22_163.pub2 is used where an overhead product comprising water is separated from a bottoms product comprising 1,2-propanediol and higher propylene glycols in a series of two to four heat integrated distillation steps, followed by a vacuum distillation step which provides 1,2-propanediol as the overhead product and a bottoms product containing higher boiling organic compounds and salts. From this bottoms product, dipropylene glycol and tripropylene glycol may be recovered as overhead products in further vacuum distillation steps.

In a preferred embodiment, step e) comprises subjecting at least a part and preferably all of the aqueous phase ($P_a$) to a catalytic hydrogenation, preferably at a temperature of from 80° C. to 140° C., more preferably from 90° C. to 120° C., prior to recovering 1,2-propanediol by distillation. The hydrogenation is preferably carried out using a supported hydrogenation catalyst comprising one or more metals from the group of Ru, Rh, Pt, Ag, Ir, Fe, Cu, Ni and Co on a support, wherein activated carbon, $SiO_2$, $TiO_2$, $ZrO_2$, $Al_2O_3$ and aluminium silicates are preferred as support materials. Preference is given to supported hydrogenation catalysts comprising ruthenium as active metal. The catalytic hydrogenation is preferably carried out at a partial hydrogen pressure of 5 to 50 bar, preferably 5 to 35 bar, more preferred 7 to 30 bar, even more preferred 8 to 25 bar. The hydrogenation catalyst may be used as a suspension or as a fixed bed, a trickle bed hydrogenation with a fixed bed catalyst being preferred. The hydrogenation can prevent problems caused by decomposition of hydrogen peroxide, which has not reacted in step a), in step e) of recovering 1,2-propanediol and dipropylene glycol. The hydrogenation also converts the by-products 1-hydroperoxy-2-propanol, 2-hydroperoxy-1-propanol and hydroxyacetone formed in step a) to 1,2-propanediol and thereby improves the yield of 1,2-propanediol.

The method of the invention can be carried out in the facility of the invention.

The facility of the invention comprises a cooled loop reactor (1) which comprises an inlet (2) for hydrogen peroxide, an inlet (3) for propene, an outlet (4) for reaction mixture, and at least one recycle stream inlet (5). The loop reactor may comprise any kind of heat exchanger (21) for effecting the cooling and preferably comprises a plate heat exchanger or a tube bundle heat exchanger which is preferably configured for reaction mixture passing through the tubes. The loop reactor typically further comprise a circulation pump (22) and a circulation conduit (23), as well as inlets for hydrogen peroxide, the propene feedstock, phase transfer catalyst and heteropolytungstate (24). When a polytungstophosphate is used as heteropolytungstate, the loop reactor may comprise inlets for phosphoric acid and for a tungstate, such as sodium tungstate. The outlet (4) for reaction mixture is preferably located at the uppermost point of the loop, which allows for operating the loop reactor (1) flooded with the liquid reaction mixture, i.e. without a continuous gas phase inside the loop reactor (1).

The facility of the invention further comprises a phase separator (6) which comprises an inlet, a first outlet for separated aqueous phase and a second outlet for separated organic phase. The inlet of the phase separator (6) is connected by a conduit (7) to the outlet (4) of the loop reactor (1) for receiving reaction mixture. The outlet for separated organic phase is preferably located at the uppermost point of the phase separator (6), which allows for operating the phase separator (6) flooded with the liquid reaction mixture, i.e. without a continuous gas phase inside the phase separator (6). The phase separator (6) preferably comprises a settler vessel. A coalescer element (not shown in the FIGURE) comprising a structured packing or a random packing with a surface wetted by the dispersed phase of the two-phase mixture may be arranged in the phase separator (6) or upstream of the phase separator (6). The phase separator (6) may also comprise an inlet for an aqueous sulfate solution (not shown in the FIGURE) which is preferably located on the upstream conduit (7) and, if a coalescer is present, is preferably located upstream of the coalescer.

The facility of the invention also comprises an oxygen desorption unit (8) which has a liquid inlet, an inlet for inert gas (25), an off-gas outlet (26) and a liquid outlet. The liquid inlet is connected to the second outlet of the phase separator (6) by a conduit (9) which comprises a first control valve (10) for receiving the separated organic phase. The liquid outlet is connected to a recycle stream inlet (5) of the loop reactor by a conduit (11) which comprises a recycle pump (12). The oxygen desorption unit may be a vessel without internals or may comprise a desorption column containing a random packing or a structured packing for carrying out desorption in trickle flow. The liquid outlet is preferably located at the bottom of the oxygen desorption unit (8) and the off-gas outlet is preferably located at the top of the oxygen desorption unit (8). The liquid inlet may be located below the inlet for inert gas but is preferably located above the inlet for inert gas to effect a counter current flow in the oxygen desorption unit (8). The oxygen desorption unit (8) may additionally comprise a demister (not shown in the FIGURE) at the off-gas outlet to prevent entrainment of liquid droplets in the off-gas. The oxygen desorption unit (8) preferably comprises a pressure retention valve (20) on the off-gas outlet to adjust and control the pressure in the oxygen desorption unit (8).

The facility of the invention further comprises a separation unit (13) which has an inlet connected to the first outlet of the phase separator (6) by a conduit (14) which comprises a second control valve (15), an outlet for separated water, an outlet for separated 1,2-propanediol and an outlet for by-products. The separation unit (13) preferably comprises a series of at least two distillation columns with a first distillation column (17), which has a bottoms outlet and an inlet providing the inlet of the separation unit (13), and a second distillation column (18). The second distillation column (18) has an inlet connected to the bottoms outlet of the first distillation column (17), an overhead product outlet for separated 1,2-propanediol and a bottoms outlet for by-products.

The facility of the invention preferably comprises an additional hydrogenation unit (19) arranged between the first outlet of the phase separator (6) and the inlet of the separation unit (13). The hydrogenation unit (19) preferably comprises a fixed bed reactor, preferably configured for trickle bed operation, for hydrogenating the separated aqueous phase with hydrogen in the presence of a heterogeneous hydrogenation catalyst.

The phase separator (6) preferably comprises a phase boundary sensor (16). Any type of phase boundary sensor known to be suitable for detecting the phase boundary between an aqueous phase and an organic phase may be used, such as a conductivity sensor or a capacitive sensor. In a first embodiment, this phase boundary sensor (16) controls the first control valve (10) to maintain a constant level of the phase boundary between the aqueous phase and the organic phase in the phase separator (6) and the second control valve (15) is a pressure retention valve. In an alternative second embodiment, the phase boundary sensor (16) controls the second control valve (10) to maintain a constant level of the phase boundary between the aqueous phase and the organic phase in the phase separator (6) and the first control valve (10) is a pressure retention valve.

The present invention will now be explained in more detail with reference to an example.

EXAMPLE

A process simulation was carried out for the method of the invention based on experimental data obtained for reaction step a) in a continuously operated laboratory mini plant. In the experiment, additional propane was fed to account for the enrichment of propane in the process when operating with a recycle of propene with the organic phase.
Preparation of Initial Epoxidation Catalyst Solution A mixture of 29 g 70% by weight hydrogen peroxide, 94 g demineralized water, 78 g 85% by weight phosphoric acid and 48 g sodium tungstate dihydrate was stirred for 2 h at room temperature. Then, a solution of 82 g of methyltri (octyl/decyl)ammonium methylsulfate (CAS No. 2387913-24-6) in 884 g Hydrosol A 200 ND (a mixture of C10 alkyl benzenes) was added and the mixture was stirred for another 2 h at room temperature. The aqueous and organic phases were then separated to provide 995 g of organic phase as initial epoxidation catalyst solution.

Reaction of Propene with Hydrogen Peroxide

The reaction of propene with hydrogen peroxide was carried out at a temperature of 80° C. and a pressure of 30 bar in a loop reactor with a loop volume of 0.45 l, a circulation pump and a heat exchanger for adjusting the reaction temperature, which was operated at a circulation rate of 130 kg h$^{-1}$. The reactor was equipped with a catalyst feed reservoir, an organic phase collection vessel equipped with a stirrer, and feed pumps for feeding liquid propene, liquid propane, an aqueous hydrogen peroxide solution and liquid from the catalyst feed reservoir. The initial epoxidation catalyst solution was charged to the catalyst feed reservoir and the aqueous phase which had been separated from the initial epoxidation catalyst solution was charged to the organic phase collection vessel. The loop initially contained reaction mixture from a previous experiment. Circulation was started and maintained at 130 kg h$^{-1}$ and the circulating mixture was heated to 80° C. Then 80 g h$^{-1}$ of propene, 50 g h$^{-1}$ of propane, 210 g h$^{-1}$ of a 15% by weight aqueous hydrogen peroxide solution containing 0.05% by weight phosphoric acid, and 320 g h$^{-1}$ of organic catalyst solution from the catalyst feed reservoir were introduced into the loop reactor, cooling the circulating mixture to maintain a reaction temperature of 80° C. A two-phase oxidation reaction mixture was removed from the loop reactor in an amount corresponding to the amounts added and 18 g h$^{-1}$ of a 9% by weight aqueous disodium sulfate solution was added to this mixture at the reactor outlet to speed up phase separation. The organic phase and the aqueous phase of the resulting mixture were separated, and the organic phase was passed to the organic phase collection vessel after depressurizing and cooling to 25° C. When 500 g of the organic phase had accumulated in the organic phase collection vessel, the content of the vessel was thoroughly mixed by stirring for 5 min at 25° C., phases were separated by settling and the organic phase was passed to the catalyst feed reservoir with the aqueous phase remaining in the organic phase collection vessel. The depressurized organic phase and the aqueous phase were analyzed after steady state operation was reached. The aqueous phase was analyzed for hydrogen peroxide by redox titration and for organic reaction products by capillary GC (25 m CP-WAX-52 CB column from Agilent, He carrier gas, temperature program starting at 50° C. with ramps of 20 K/min to 90° C., 10 K/min to 220° C. and 5 K/min to 235° C., FID detector).
Process Simulation A process simulation was carried out with the program Aspen Plus® of Aspen Technology for the process units loop reactor (1), phase separator (6), oxygen desorption (8) and recycle of organic phase through conduit (11) of a facility as shown in the FIGURE, based on the experimental analysis data for the products formed in the reaction step. The calculation was carried out for operating the loop reactor at 80° C. and 25 bar, the phase separator at 40° C. and 23 bar and the oxygen desorption at 40° C. and 9 bar, assuming a hydrogen peroxide conversion of 96.2% and a decomposition of 1.5% of the fed hydrogen peroxide to oxygen in the loop reactor. Feeds to the loop reactor were 100 kg/h of a propene feedstock containing 97.1 mol-% propene and 2.9 mol-% propane, 638 kg/h of a 15% by weight aqueous hydrogen peroxide solution, 0.36 kg/h of 85% by weight phosphoric acid, 0.26 kg/h of a 50% by weight solution of sodium tungstate, 0.24 kg/h of methyltri(octyl/decyl)ammonium methylsulfate and the oxygen depleted organic phase from the oxygen desorption unit (8). 4.54 kg/h of nitrogen were introduced into the oxygen desorption unit (8). Table 1 shows the flow rates and contents of selected components calculated for stream A of the reaction mixture exiting the loop reactor (1) through conduit (7), stream B of the aqueous phase exiting the phase separator (6) through conduit (14), stream C of the organic phase exiting the phase separator (6) through conduit (9), stream D of the oxygen depleted organic phase recycled from the oxygen desorption unit (8) to the loop reactor (1) through conduit (11) and stream E of the off-gas exiting the process through the off-gas outlet (26). The process simulation shows that no gas phase forms in the loop reactor (1) or the phase separator (6) because the contents of propene and oxygen in the reaction mixture do not exceed the solubility limit for the organic phase at the operating pressure. The process simulation also shows that only 3% of the propene introduced with the propene feedstock is purged with the off-gas stream along with a fraction of 14% of the oxygen dissolved in the organic phase of the reaction mixture.

TABLE 1

| Flow rates in kg/h and content in % by weight calculated for streams A to E | | | | |
| --- | --- | --- | --- | --- |
| Stream | A | B | C | D | E |
| Flow rate in kg/h | 1894 | 720.7 | 1173.3 | 1166.6 | 11.3 |
| Nitrogen | 0.45 | | 0.73 | 0.73 | 40.4 |
| Oxygen | 0.25 | | 0.41 | 0.35 | 6.0 |
| Propene | 6.47 | | 10.45 | 10.25 | 26.6 |
| Propane | 6.38 | | 10.29 | 10.09 | 26.6 |
| Water | 28.97 | 76.12 | | | |
| Hydrosol solvent | 40.81 | | 65.78 | 66.25 | 0.2 |
| 1,2-Propane diol | 7.54 | 19.81 | | | |
| Dipropylene glycol | 0.93 | 2.44 | | | |

LIST OF REFERENCE SIGNS

1 Cooled loop reactor
2 Inlet for hydrogen peroxide
3 Inlet for propene
4 Outlet for reaction mixture
5 Recycle stream inlet
6 Phase separator
7 Conduit connecting the loop reactor (1) with the phase separator (6)
8 Oxygen desorption unit
9 Conduit connecting the phase separator (6) with the oxygen desorption unit (8)
10 First control valve
11 Conduit connecting the oxygen desorption unit (8) with the loop reactor (1)
12 Recycle pump
13 Separation unit
14 Conduit connecting the phase separator (6) with the separation unit (13)
15 Second control valve
16 Phase boundary sensor
17 First distillation column
18 Second distillation column
19 Hydrogenation unit
20 Pressure retention valve
21 Heat exchanger
22 Circulation pump
23 Circulation conduit
24 Inlet for heteropolytungstate
25 Inlet for inert gas
26 Off-gas outlet

The invention claimed is:

1. A method for the preparation of 1,2-propanediol, comprising:
  a) reacting propene with hydrogen peroxide at a temperature of from 50 to 110° C. in the presence of a catalyst mixture, comprising a phase transfer catalyst and a heteropolytungstate, in a liquid reaction mixture comprising an aqueous phase with a maximum apparent pH of 6 and an organic phase comprising an alkylaromatic hydrocarbon solvent;
  b) separating the liquid reaction mixture obtained in a) into an aqueous phase ($P_a$) comprising 1,2-propanediol and an organic phase ($P_o$) comprising non-reacted propene, the alkylaromatic hydrocarbon solvent, and dissolved oxygen from hydrogen peroxide decomposition;
  c) contacting the organic phase ($P_o$) separated in b) with a stream of a non-flammable gas at a flow rate of the non-flammable gas, a temperature, and a pressure effecting desorption of from 10 to 75% of the dissolved oxygen in the organic phase ($P_o$) into the stream of the non-flammable gas, to provide an oxygen depleted organic phase ($P_a$) and an off-gas comprising the non-flammable gas and desorbed propene and oxygen;
  d) recycling at least a part of the oxygen depleted organic phase ($P_a$) to the reaction a); and
  e) recovering the 1,2-propanediol from the aqueous phase ($P_a$);
  wherein a mass ratio of the alkylaromatic hydrocarbon solvent introduced to a) to the hydrogen peroxide introduced to a) is from 4:1 to 30:1; and
  wherein a) and b) are each carried out in a vessel flooded by the liquid reaction mixture at a pressure high enough to suppress desorption of gas from the liquid reaction mixture.

2. The method of claim 1, wherein a) to d) are carried out continuously.

3. The method of claim 2, wherein in a), a concentration of the hydrogen peroxide in the aqueous phase is from 0.1 to 5% by weight.

4. The method of claim 1, wherein a molar ratio of the propene introduced to a) to the hydrogen peroxide introduced to a) is from 1.2:1 to 5:1.

5. The method of claim 1, wherein the alkylaromatic hydrocarbon solvent comprises more than 50% by weight of at least one alkylated aromatic hydrocarbon having from 7 to 12 carbon atoms.

6. The method of claim 1, wherein in c), the non-flammable gas is passed through the organic phase ($P_o$).

7. The method of claim 1, wherein in c), the desorption is carried out with counter current flow of the non-flammable gas and the organic phase ($P_o$).

8. The method of claim 1, wherein in c), the flow rate of the non-flammable gas, the temperature, and the pressure are adjusted to provide an oxygen concentration in the off-gas of from 1 to 11 mol-%.

9. The method of claim 1, wherein nitrogen is used as the non-flammable gas.

10. The method of claim 1, wherein a) is carried out with a propene feedstock containing from 1 to 8 mol-% of propane, and
  wherein in c), the flow rate of the non-flammable gas, the temperature, and the pressure are adjusted to provide the off-gas with a mass ratio of propane to a combined amount of propane and propene of from 0.2 to 0.7.

11. The method of claim 1, wherein a) is conducted continuously in a loop reactor comprising fixed internals in a tubular section, and the liquid reaction mixture is passed through the loop reactor at a flow rate sufficient to provide turbulent flow at said fixed internals.

12. The method of claim 1, wherein the heteropolytungstate is a polytungstophosphate.

13. The method of claim 1, wherein the phase transfer catalyst is at least one selected from the group consisting of a tertiary amine, a tertiary ammonium salt, and a quaternary ammonium salt, and wherein the tertiary amine, the tertiary ammonium salt, and the quaternary ammonium salt each comprises in total at least 12 carbon atoms.

14. The method of claim 13, wherein the phase transfer catalyst comprises a tertiary or quaternary ammonium ion having the structure $R^1R^2R^3NR^{4+}$, wherein $R^1$, $R^2$, and $R^3$ are the same or different and are each an alkyl group having from 8 to 10 carbon atoms, and $R^4$ is hydrogen or methyl.

15. A facility for preparing 1,2-propanediol, comprising:

a cooled loop reactor comprising an inlet for hydrogen peroxide, an inlet for propene, an outlet for a reaction mixture, and at least one recycle stream inlet;

a phase separator comprising an inlet, a first outlet for a separated aqueous phase and a second outlet for a separated organic phase, the inlet being connected by a first conduit to the outlet of the cooled loop reactor for receiving the reaction mixture;

an oxygen desorption unit having a liquid inlet, an inlet for inert gas, an off-gas outlet, and a liquid outlet, the liquid inlet being connected by a second conduit, comprising a first control valve, to the second outlet of the phase separator for receiving the separated organic phase, and the liquid outlet being connected by a third conduit comprising a recycle pump to the at least one recycle stream inlet of the cooled loop reactor; and a separation unit, having an inlet connected by a fourth conduit, comprising a second control valve, to the first outlet of the phase separator, an outlet for separated water, an outlet for separated 1,2-propanediol, and an outlet for by-products.

16. The facility of claim 15, wherein the phase separator comprises a phase boundary sensor controlling the first control valve, and the second control valve is a pressure retention valve.

17. The facility of claim 15, wherein the phase separator comprises a phase boundary sensor controlling the second control valve, and the first control valve is a pressure retention valve.

18. The facility of claim 15, wherein the separation unit comprises a first distillation column, the first distillation column having the inlet of said separation unit and a bottoms outlet, and a second distillation column, the second distillation column having an inlet connected to the bottoms outlet of the first distillation column, an overhead product outlet for the separated 1,2 propanediol and a bottoms outlet for the by-products.

19. The facility of claim 18, comprising a hydrogenation unit arranged between the first outlet of the phase separator and the inlet of the separation unit.

20. The facility of claim 15, further comprising a pressure retention valve on the off-gas outlet of the oxygen desorption unit.

* * * * *